(12) United States Patent
Schaub et al.

(10) Patent No.: US 8,791,297 B2
(45) Date of Patent: Jul. 29, 2014

(54) PROCESS FOR PREPARING FORMIC ACID BY REACTION OF CARBON DIOXIDE WITH HYDROGEN

(75) Inventors: Thomas Schaub, Neustadt (DE); Donata Maria Fries, Mannheim (DE); Rocco Paciello, Bad Dürkheim (DE); Klaus-Dieter Mohl, Hockenheim (DE); Martin Schäfer, Grünstadt (DE); Stefan Rittinger, Mannheim (DE); Daniel Schneider, Mannheim (DE)

(73) Assignee: BASF SE (DE)

( * ) Notice: Subject to any disclaimer, the term of this patent is extended or adjusted under 35 U.S.C. 154(b) by 605 days.

(21) Appl. No.: 13/172,123

(22) Filed: Jun. 29, 2011

(65) Prior Publication Data

US 2011/0319658 A1    Dec. 29, 2011

Related U.S. Application Data

(60) Provisional application No. 61/359,405, filed on Jun. 29, 2010.

(51) Int. Cl.
| | | |
|---|---|---|
| *C07C 51/44* | (2006.01) | |
| *C07C 53/02* | (2006.01) | |
| *C07C 51/15* | (2006.01) | |
| *C07C 51/48* | (2006.01) | |
| *C07C 51/487* | (2006.01) | |

(52) U.S. Cl.
CPC .................. *C07C 53/02* (2013.01); *C07C 51/15* (2013.01); *C07C 51/48* (2013.01); *C07C 51/487* (2013.01)
USPC ........................................................ 562/609

(58) Field of Classification Search
CPC ........ C07C 53/02; C07C 51/15; C07C 51/48; C07C 51/487
USPC ........................................................ 562/609
See application file for complete search history.

(56) References Cited

U.S. PATENT DOCUMENTS

| | | | |
|---|---|---|---|
| 4,855,496 A | 8/1989 | Anderson et al. | |
| 4,879,070 A | 11/1989 | Kent | |
| 2008/0097126 A1 | 4/2008 | Karl et al. | |
| 2010/0063320 A1 | 3/2010 | Challand et al. | |
| 2010/0331573 A1 | 12/2010 | Schaub et al. | |
| 2011/0319657 A1 | 12/2011 | Schneider et al. | |
| 2012/0022290 A1 | 1/2012 | Schaub et al. | |

FOREIGN PATENT DOCUMENTS

| | | |
|---|---|---|
| CA | 2809297 A1 | 3/2012 |
| DE | 4431233 A1 | 3/1995 |
| EP | 0 095 321 A2 | 11/1983 |
| EP | 0126524 A1 | 11/1984 |
| EP | 0151510 A1 | 8/1985 |
| EP | 0181078 A1 | 5/1986 |
| EP | 0329337 A2 | 8/1989 |
| EP | 0 357 243 A2 | 3/1990 |
| JP | 60209260 | 10/1985 |
| JP | 62-500303 | 2/1987 |
| JP | 2010521533 A | 6/2010 |
| JP | 2013530195 A | 7/2013 |
| WO | WO-2006/021411 A1 | 3/2006 |
| WO | WO-2008/116799 A1 | 10/2008 |
| WO | WO-2010/149507 A2 | 12/2010 |
| WO | PCT/EP2011/058758 | 5/2011 |
| WO | PCT/EP2011/060269 | 5/2011 |
| WO | PCT/EP2011/060770 | 5/2011 |

OTHER PUBLICATIONS

Japanese Office Action from corresponding Japanese Patent Application No. 13/172,123, Feb. 17, 2014.
U.S. Appl. No. 61/316,841.
U.S. Appl. No. 61/359,382.
U.S. Appl. No. 61/359,401.
Boddien, A., "Hydrogen Generation at Ambient Conditions: Application in Fuel Cells," ChemSusChem (2008), vol. 1, pp. 751-758.
Enthaler, S., "Carbon Dioxide—The Hydrogen-Storage Material of the Future?" ChemSusChem (2008), vol. 1, pp. 801-804.
Fellay, C., et al., "A Viable Hydrogen-Storage System Based on Selective Formic Acid Decomposition with a Ruthenium Catalyst," Angew. Chem. (2008), vol. 120, pp. 4030-4032.
Fellay, C., et al., "Selective Formic Acid Decomposition for High-Pressure Hydrogen Generation: A Mechanistic Study," Chem. Eur. J. (2009), vol. 15, pp. 3752-3760.
Fukuzumi, S., et al., "Efficient Catalytic Decomposition of Formic Acid for the Selective Generation of H1 and H/D Exchange with a Water-Soluble Rhodium Complex in Aqueous Solution," ChemSusChem (2008), vol. 1, pp. 827-834.
Jessop, P.G., "Homogeneous Hydrogenation of Carbon Dioxide," Chemical Reviews (Mar./Apr. 1995), vol. 95, No. 2, pp. 259-272.

(Continued)

*Primary Examiner* — Yevegeny Valenrod
(74) *Attorney, Agent, or Firm* — Drinker Biddle & Reath LLP

(57) ABSTRACT

A process for preparing formic acid by reaction of carbon dioxide (1) with hydrogen (2) in a hydrogenation reactor (I) in the presence of

- a catalyst comprising an element of group 8, 9 or 10 of the Periodic Table,
- a tertiary amine comprising at least 12 carbon atoms per molecule and
- a polar solvent comprising one or more monoalcohols selected from among methanol, ethanol, propanols and butanols and also water, to form formic acid/amine adducts as intermediates which are subsequently thermally dissociated, with work-up of the output (3) from the hydrogenation reactor (I) in a plurality of process steps, where a tertiary amine-comprising stream (13) from the work-up is used as selective solvent for the catalyst, is proposed.

15 Claims, 3 Drawing Sheets

(56) References Cited

OTHER PUBLICATIONS

Jessop, P.G., "Homogeneous Hydrogenation of Carbon Dioxide," The Handbook of Homogeneous Hydrogenation, Hrsg.: J.G. de Vries, C.J. Elsevier (2007), vol. 1, Wiley-VCH Verlag GmbH & Co. KGaA, pp. 489-511.

Jessop, P.G., et al., "Recent advances in the homogeneous hydrogenation of carbon dioxide," Coordination Chemistry Reviews (2004), vol. 248, pp. 2425-2442.

Joó, F., "Breakthroughs in Hydrogen Storage—Formic Acid as a Sustainable Storage Material for Hydrogen," ChemSusChem (2008), vol. 1, pp. 805-808.

Leitner, W., "Kohlendioxid als Rohstoff am Beispiel der Synthese von Ameisensáure und ihren Derivaten," Angewandte Chemie (1995), vol. 107, pp. 2391-2405.

Loges, B., et al., "Kontrollierte Wasserstofferzeugung aus Ameisensáure-Amin-Addukten bei Raumtemperatur und direkte Nutzung in $H_2/O_2$-Brennstoffzellen," Angew. Chem. (2008), vol. 120, pp. 4026-4029.

PROCESS FOR PREPARING FORMIC ACID BY REACTION OF CARBON DIOXIDE WITH HYDROGEN

RELATED APPLICATIONS

This patent application claims the benefit of pending U.S. provisional patent application Ser. No. 61/359,405 filed Jun. 29, 2010 incorporated in its entirety herein by reference.

BACKGROUND OF THE INVENTION

The invention relates to a process for preparing formic acid by reaction of carbon dioxide with hydrogen in a hydrogenation reactor in the presence of a catalyst comprising an element of group 8, 9 or 10 of the Periodic Table, a tertiary amine and a polar solvent to form formic acid/amine adducts as intermediates which are subsequently thermally dissociated.

Fe, Co, Ni, Ru, Rh, Pd, Os, Ir and/or Pt. The catalyst preferably comprises Ru, Rh, Pd, Os, Ir and/or Pt, particularly preferably Ru, Rh and/or Pd and very particularly preferably Ru.

To make an economical process possible, the catalyst used has to be separated off ideally completely from the product stream and recirculated to the reaction, for two reasons:

(1) large losses of the expensive catalyst would incur considerable additional costs and would be prohibitive for economical operation of the process.

(2) in the thermal dissociation of the formic acid/amine adducts, very little catalyst should be present since in the absence of a $CO_2$ and/or $H_2$ pressure this also catalyzes the reverse reaction and thus leads to losses of the formic acid formed.

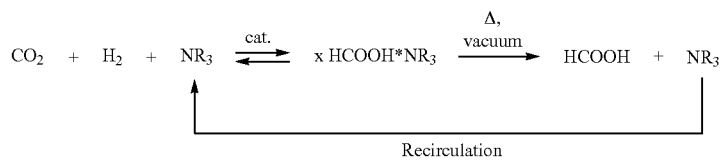

Formation of formic acid by $CO_2$ hydrogenation (x = 0.4-3)

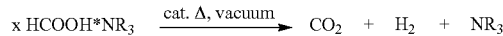

Decomposition of formic acid/amine adducts in the presence of a catalyst (x=0.4–3)

Adducts of formic acid and tertiary amines can be thermally dissociated into free formic acid and tertiary amine and therefore serve as intermediates in the preparation of formic acid.

Formic acid is an important and versatile product. It is used, for example, for acidification in the production of animal feeds, as preservative, as disinfectant, as auxiliary in the textile and leather industry, as a mixture with its salts for deicing aircraft and runways and also as synthetic building block in the chemical industry.

The abovementioned adducts of formic acid and tertiary amines can be prepared in various ways, for example (i) by direct reaction of tertiary amine with formic acid, (ii) by hydrolysis of methyl formate to form formic acid in the presence of the tertiary amine or (iii) by catalytic hydration of carbon monoxide or hydrogenation of carbon dioxide to form formic acid in the presence of the tertiary amine. The latter process of catalytic hydrogenation of carbon dioxide has the particular advantage that carbon dioxide is available in large quantities and is flexible in terms of source.

An industrially promising process appears to be, in particular, the catalytic hydrogenation of carbon dioxide in the presence of amines (W. Leitner, Angewandte Chemie 1995, 107, pages 2391 to 2405; P. G. Jessop, T. Ikariya, R. Noyori, Chemical Reviews 1995, 95, pages 259 to 272). The adducts of formic acid and amines formed here can be thermally dissociated into formic acid and the amine used, which can be recirculated to the hydrogenation.

The catalyst necessary for the reaction comprises one or more elements from group 8, 9 or 10 of the Periodic Table, i.e.

The transition metal-catalyzed decomposition of formic acid has been described comprehensively, especially recently: C. Fellay, N. Yan, P. J. Dyson, G. Laurenczy Chem. Eur. J. 2009, 15, 3752-3760; C. Fellay, P. J. Dyson, G. Laurenczy Angew. Chem. 2008, 120, 4030-4032; B. Loges, A. Boddien, H. Junge, M. Beller Angew. Chem. 2008, 120, 4026-4029; F. Joó ChemSusChem 2008, 1, 805-808; S. Enthaler ChemSusChem 2008, 1, 801-804; S. Fukuzumi, T. Kobayashi, T. Suenobu ChemSusChem 2008, 1, 827-834; A. Boddien, B. Loges, H. Junge, M. Beller ChemSusChem 2008, 1, 751-758.

The catalysts used here are in principle also suitable in principle for the hydrogenation of $CO_2$ to formic acid (P. G. Jessop, T. Ikariya, R. Noyori Chem. Rev. 1995, 95, 259-272; P. G. Jessop, F. Joó, C. C. Tai Coord. Chem. Rev. 2004, 248, 2425-2442; P. G. Jessop, Homogeneous Hydrogenation of Carbon Dioxide, in: The Handbook of Homogeneous Hydrogenation, Hrsg.: J. G. de Vries, C. J. Elsevier, Volume 1, 2007, Wiley-VCH, pp. 489-511). Thus, the hydrogenation catalysts have to be separated off before the thermal dissociation in order to prevent the undesirable decomposition of formic acid.

WO 2008/116,799 discloses a process for the hydrogenation of carbon dioxide in the presence of a catalyst which comprises a transition metal of transition group VIII (groups 8, 9, 10) and is suspended or homogeneously dissolved in a solution, a tertiary amine having at least one hydroxyl group and a polar solvent to form an adduct of formic acid and the tertiary amine. The hydroxyl group(s) in the tertiary amine enable an increased carbon dioxide solubility compared to the triethylamine which is usually used to be achieved. As preferred homogeneous catalysts, mention may be made of $RuH_2L_4$ having monodentate phosphorus-based ligands L and $RuH_2(LL)_2$ having bidentate phosphorus-based ligands LL and particularly preferably $RuH_2[P(C_6H_5)_3]_4$. As polar solvents, mention may be made of alcohols, ethers, sulfolanes, dimethyl sulfoxide and amides whose boiling point at atmospheric pressure is at least 5° C. above that of formic acid. The tertiary amines which are preferably to be used also have a boiling point above that of formic acid. Since no phase separation takes place, the work-up of the entire reaction product mixture is carried out by distillation, optionally after prior removal of the catalyst, in which the adduct of formic acid and the tertiary amine which is formed is thermally dissociated and the formic acid liberated is isolated as overhead product. The bottom product comprising tertiary amine, polar solvent and optionally catalyst is recirculated to the hydrogenation stage.

A disadvantage of this process is the introduction of the entire liquid reaction product mixture into the apparatus for thermal dissociation and distillation, optionally after prior specific removal of the homogeneous catalyst by means of a separate process step, for example an extraction, adsorption or ultrafiltration step. The apparatus for the thermal dissociation and distillation consequently has to be made larger and more complex both in terms of the higher liquid throughput and the more specific separation properties, which is reflected, inter alia, in the capital costs (for example via engineering input, material, space requirement). In addition, the higher liquid throughput also results in a higher energy usage.

However, the fundamental work on the catalytic hydrogenation of carbon dioxide to form formic acid was carried out as early as the 1970s and 1980s. The processes of BP Chemicals Ltd filed as the patents EP 0 095 321 A, EP 0 151 510 A and EP 0 181 078 A may be considered to result therefrom. All three documents describe the hydrogenation of carbon dioxide in the presence of a homogeneous catalyst comprising a transition metal of transition group VIII (groups 8, 9, 10), a tertiary amine and a polar solvent to form an adduct of formic acid and the tertiary amine. As preferred homogeneous catalysts, EP 0 095 321 A and EP 0 181 078 A in each case make mention of ruthenium-based carbonyl-, halide- and/or triphenylphosphine-comprising complex catalysts and EP 0 151 510 A mentions rhodium-phosphine complexes. Preferred tertiary amines are $C_1$-$C_{10}$-trialkylamines, in particular the short-chain $C_1$-$C_4$-trialkylamines, and also cyclic and/or bridged amines such as 1,8-diazabicyclo[5.4.0]undec-7-ene, 1,4-diazabicyclo[2.2.2]octane, pyridine or picolines. The hydrogenation is carried out at a carbon dioxide partial pressure of up to 6 MPa (60 bar), a hydrogen partial pressure of up to 25 MPa (250 bar) and a temperature from about room temperature to 200° C.

EP 0 095 321 A and EP 0 151 510 A teach the use of an alcohol as polar solvent. However, since primary alcohols tend to form formic esters (organic formates), secondary alcohols, in particular isopropanol, are preferred. In addition, the presence of water is described as advantageous. According to the examples in EP 0 095 321 A, the reaction product mixture is worked up by directly subsequent two-stage distillation in which the low boilers alcohol, water, tertiary amine are separated off in the first stage and the adduct of formic acid and the tertiary amine is separated off at the top under vacuum conditions in the second stage. EP 0 151 510 A likewise teaches a work-up by distillation, but with reference to EP 0 126 524 A with subsequent replacement of the tertiary amine in the adduct which has been separated off by distillation by a weaker, less volatile nitrogen base before thermal cleavage of the adduct in order to aid or make possible the subsequent thermal dissociation to produce free formic acid.

EP 0 181 078 A teaches the targeted choice of the polar solvent on the basis of three essential criteria which have to be fulfilled at the same time:
(i) the homogeneous catalyst has to be soluble in the polar solvent;
(ii) the polar solvent must not have an adverse effect on the hydrogenation; and
(iii) the adduct of formic acid and the tertiary amine which is formed should be able to be readily separated off from the polar solvent.

As particularly suitable polar solvents, mention is made of various glycols and phenylpropanols.

According to the teaching of EP 0 181 078 A, the work-up of the reaction product mixture is carried out by firstly separating off the gaseous components (in particular unreacted starting materials hydrogen and carbon dioxide) at the top of an evaporator and separating off the homogeneous catalyst dissolved in the polar solvent at the bottom and recirculating them to the hydrogenation stage. The adduct of formic acid and the tertiary amine is subsequently separated off from the remaining liquid phase comprising the adduct of formic acid and the tertiary amine, free tertiary amine and possibly water and the remaining part of the liquid phase comprising the free tertiary amine and possibly water is recirculated to the hydrogenation stage. The separation can be effected by distillation or phase separation of the two-phase system (decantation).

A further significant teaching of EP 0 181 078 A is the subsequent, absolutely necessary replacement of the tertiary amine in the adduct which has been separated off by a weaker, less volatile nitrogen base before the adduct is thermally dissociated in order to aid or make possible the subsequent thermal dissociation to produce free formic acid. As particularly suitable weaker nitrogen bases, mention is made of imidazole derivatives such as 1-n-butylimidazole.

A disadvantage of the process of EP 0 181 078 A is the very complicated, four-stage work-up of the reaction product mixture by
(i) separating off the gaseous components and also the homogeneous catalyst and the polar solvent in an evaporator and recirculating them to the hydrogenation stage;
(ii) separating off the adduct of formic acid and the tertiary amine in a distillation column or a phase separator and recirculating the remaining liquid stream to the hydrogenation stage;
(iii) replacing the tertiary amine in the adduct of formic acid and the tertiary amine by a weaker, less volatile nitrogen base in a reaction vessel having a superposed distillation column and recirculating the tertiary amine liberated to the hydrogenation stage; and
(iv) thermally dissociating the adduct of formic acid and the weaker nitrogen base and recirculating the weaker nitrogen base liberated to the base replacement stage.

A further, important disadvantage of the process of EP 0 181 078 A and also of the processes of EP 0 095 321 A and EP 0 151 510 A is the fact that the adduct of formic acid and the tertiary amine partly redissociates into carbon dioxide and hydrogen in the presence of the homogeneous catalyst during the work-up in the evaporator. As a solution to this problem, EP 0 329 337 A proposes the addition of a decomposition inhibitor which reversibly inhibits the homogeneous catalyst. As preferred decomposition inhibitors, mention is made of carbon monoxide and oxidants. However, disadvantages of this are the introduction of further substances into the overall process and the necessity of reactivating the inhibited homogeneous catalyst before it is used further.

EP 0 357 243 A, too, addresses the disadvantage of the partial redissociation of the adduct of formic acid and the tertiary amine in the process of EP 0 181 078 A by joint work-up of the reaction product mixture in the evaporator. The process proposed in EP 0 357 243 A teaches the use of a homogeneous catalyst comprising a transition metal of transition group VIII (groups 8, 9, 10), a tertiary amine and two different solvents, namely a nonpolar, inert solvent and a polar, inert solvent, which form two immiscible liquid phases in the catalytic hydrogenation of carbon dioxide to form an adduct of formic acid and tertiary amine. As nonpolar solvents, mention is made of aliphatic and aromatic hydrocarbons but also of phosphines having aliphatic and/or aromatic hydrocarbon radicals. Polar solvents mentioned are water, glycerol, alcohols, polyols, sulfolanes and mixtures thereof, with water being preferred. The homogeneous catalyst dissolves in the nonpolar solvent and the adduct of formic acid and tertiary amine dissolves in the polar solvent. After the reaction is complete, the two liquid phases are separated, for example by decantation, and the nonpolar phase comprising the homogeneous catalyst and the nonpolar solvent is recirculated to the hydrogenation stage. The polar phase comprising the adduct of formic acid and tertiary amine and the polar solvent is then subjected to an absolutely necessary replacement of the tertiary amine in the adduct by a weaker, less volatile nitrogen base before thermal dissociation of the adduct in order to aid or make possible the subsequent thermal dissociation to produce free formic acid. In a manner analogous to EP 0 181 078 A, imidazole derivatives such as 1-n-butylimidazole are also mentioned here as particularly suitable weaker nitrogen bases.

A disadvantage of the process of EP 0 357 243 A is the very complicated, three-stage work-up of the reaction product mixture by (i) separating the two liquid phases and recirculating the phase comprising the homogeneous catalyst and the nonpolar solvent to the hydrogenation stage;
(ii) replacing the tertiary amine in the adduct of formic acid and the tertiary amine of the other phase by a weaker, less volatile nitrogen base in a reaction vessel with superposed distillation column and recirculating the tertiary amine liberated to the hydrogenation stage; and
(iii) thermally dissociating the adduct of formic acid and the weaker nitrogen base and recirculating the weaker nitrogen base liberated to the base replacement stage.

A further disadvantage of the process of EP 0 357 243 A is the use of two solvents and thus introduction of a further substance into the overall process.

As an alternative, EP 0 357 243 A also discloses the possibility of using only one solvent. In this case, the addition of the polar solvent in which the adduct of formic acid and the tertiary amine would otherwise dissolve is omitted. The sole solvent used here is the nonpolar solvent which dissolves the homogeneous catalyst. However, this alternative also has the disadvantage of the very complicated, three-stage work-up as described above.

DE 44 31 233 A likewise describes the hydrogenation of carbon dioxide in the presence of a catalyst comprising a transition metal of transition group VIII (groups 8, 9, 10), a tertiary amine and a polar solvent and water to form an adduct of formic acid and the tertiary amine, in which, however, the catalyst is present in heterogeneous form and the active component is applied to a inert support. Preferred tertiary amines are $C_1$-$C_8$-trialkylamines, polyamines having from 2 to 5 amino groups, aromatic nitrogen heterocycles such as pyridine or N-methylimidazole and also cyclic and/or bridged amines such as N-methylpiperidine, 1,8-diazabicyclo[5.4.0]undec-7-ene or 1,4-diazabicyclo[2.2.2]octane. As suitable polar solvents, mention is made of the low-boiling $C_1$-$C_4$-monoalcohols, and, in a manner analogous to EP 0 095 321 A, secondary alcohols are preferred. The hydrogenation is carried out at a total pressure of from 4 to 20 MPa (from 40 to 200 bar) and a temperature of from 50 to 200° C. For the work-up of the adduct of formic acid and tertiary amine which is formed, DE 44 31 233 A teaches the use of known methods with explicit reference to the work-up with replacement of the tertiary amine in the adduct of formic acid and the tertiary amine by a weaker, less volatile nitrogen base as disclosed in EP 0 357 243 A. In a manner analogous to the process of EP 0 357 243 A, the process of DE 44 31 233 A also has the disadvantage of the very complicated, three-stage work-up of the reaction product mixture.

BRIEF SUMMARY OF THE INVENTION

It was an object of the present invention to provide a process for preparing formic acid by hydrogenation of carbon dioxide, which does not have the abovementioned disadvantages of the prior art or suffers from them only to a significantly reduced extent and which leads to concentrated formic acid in a high yield and high purity. Furthermore, the process should be able to be carried out in a simple manner or at least a simpler manner than is described in the prior art, in particular by means of a simpler process concept for working up the output from the hydrogenation reactor, simpler process stages, a reduced number of process stages or simpler apparatuses. In addition, the process should also be able to be carried out with the lowest possible consumption of energy.

The work-up of the output from the hydrogenation reactor should, in particular, be carried out using exclusively the materials present in the process, without additional auxiliaries, and these should be able to be completely or largely completely recycled in the process.

The object is achieved by a process for preparing formic acid by reaction of carbon dioxide with hydrogen in a hydrogenation reactor in the presence of a catalyst comprising an element of group 8, 9 or 10 of the Periodic Table,
a tertiary amine comprising at least 12 carbon atoms per molecule and
a polar solvent comprising one or more monoalcohols selected from among methanol, ethanol, propanols and butanols and also water, to form formic acid/amine adducts as intermediates which are subsequently thermally dissociated,
where a tertiary amine which has a boiling point at least 5° C. higher than that of formic acid and
two liquid phases are formed in the hydrogenation, namely a lower phase which comprises predominantly the polar solvent and in which the formic acid/amine adducts are present in enriched form and an upper phase which comprises predominantly the tertiary amine and in which the catalyst is present in enriched form, wherein the work-up of the output from the hydrogenation reactor is carried out by the following process steps:

1) separation of the two liquid phases from the hydrogenation reactor in a phase separation vessel, recirculation of the upper phase from the phase separation vessel to the hydrogenation reactor and passing-on of the lower phase from the phase separation vessel to an extraction apparatus in which 2) residues of catalyst are extracted with the same tertiary amine which was used in the hydrogenation and the catalyst-laden tertiary amine is recycled to the hydrogenation reactor and the catalyst-free stream of polar solvent loaded with the formic acid/amine adducts is passed on to a distillation unit in which
3) the polar solvent is separated off as overhead stream and recycled to the hydrogenation reactor to give a stream which
4) is separated in a phase separation vessel into an upper phase comprising predominantly the tertiary amine and a lower phase comprising predominantly the formic acid/amine adducts, where
5) the lower phase from the phase separation vessel is fed to a thermal dissociation unit and dissociated therein into a stream which comprises the tertiary amine and is recirculated to the phase separation vessel and pure formic acid and a stream comprising the tertiary amine is conveyed from the phase separation vessel into the extraction apparatus as selective solvent for the catalyst.

A BRIEF DESCRIPTION OF THE FIGURES

DETAILED DESCRIPTION OF THE INVENTION

Figure 1:
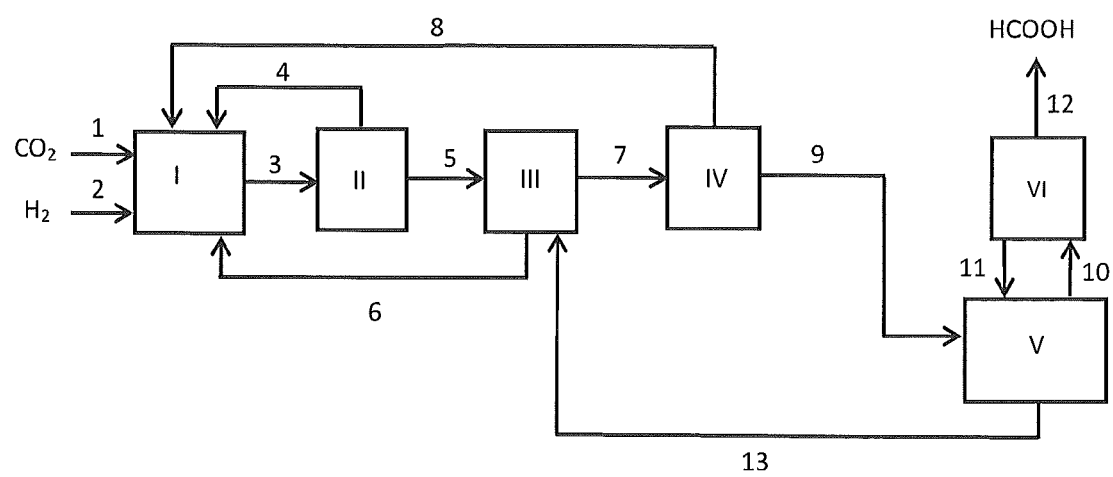
FIG. 1 illustrates a block diagram of a preferred embodiment of the process of the invention.

The catalyst to be used in the hydrogenation of carbon dioxide in the process of the invention is preferably a homogeneous catalyst. It comprises an element of group 8, 9 or 10 of the Periodic Table, i.e. Fe, Co, Ni, Ru, Rh, Pd, Os, Ir and/or Pt. The catalyst preferably comprises Ru, Rh, Pd, Os, Ir and/or Pt, particularly preferably Ru, Rh and/or Pd, and very particularly preferably Ru.

The abovementioned elements are homogeneously dissolved in the form of complex-like compounds in the reaction mixture. The homogeneous catalyst should be selected so that it is present in enriched form together with the tertiary amine in the liquid phase (B). For the present purposes, "in enriched form" means a partition coefficient of the homogeneous catalyst P=[concentration of homogeneous catalyst in liquid phase (B)]/[concentration of homogeneous catalyst in liquid phase (A)]

of >1. The choice of the homogeneous catalyst is generally made by means of a simple test in which the partition coefficient of the desired homogeneous catalyst under the planned process conditions is determined experimentally.

Liquid phase (A) is here the lower phase from the phase separation vessel in process step 1).

Owing to their good solubility in tertiary amines, preference is given to using a metal-organic complex comprising an element of group 8, 9 or 10 of the Periodic Table and at least one phosphine group having at least one unbranched or branched, acyclic or cyclic, aliphatic radical having from 1 to 12 carbon atoms, where individual carbon atoms can also be substituted by >P—, as homogeneous catalysts in the process of the invention. Branched cyclic aliphatic radicals thus also include radicals such as —$CH_2$—$C_6H_{11}$. Suitable radicals are, for example, methyl, ethyl, 1-propyl, 2-propyl, 1-butyl, 2-butyl, 1-(2-methyl)propyl, 2-(2-methyl)propyl, 1-pentyl, 1-hexyl, 1-heptyl, 1-octyl, 1-nonyl, 1-decyl, 1-undecyl, 1-dodecyl, cyclopentyl, cyclohexyl, cycloheptyl and cyclooctyl, methylcyclopentyl, methylcyclohexyl, 1-(2-methyl)pentyl 1-(2-ethyl)hexyl, 1-(2-propyl)heptyl and norbonyl. The unbranched or branched, acyclic or cyclic, aliphatic radical preferably comprises at least 1 and preferably not more than 10 carbon atoms. In the case of an exclusively cyclic radical in the abovementioned sense, the number of carbon atoms is from 3 to 12 and preferably at least 4 and also preferably not more than 8. Preferred radicals are ethyl, 1-butyl, sec-butyl, 1-octyl and cyclohexyl.

The phosphine group can comprise one, two or three of the abovementioned unbranched or branched, acyclic or cyclic, aliphatic radicals. These can be identical or different. The phosphine group preferably comprises three of the abovementioned unbranched or branched, acyclic or cyclic, aliphatic radicals and particular preference is given to all three radicals being identical. Preferred phosphines are P(n-$C_nH_{2n+1}$)$_3$ where n is from 1 to 10, particularly preferably tri-n-butylphosphine, tri-n-octylphosphine and 1,2-bis(dicyclohexylphosphino)ethane.

As mentioned above, individual carbon atoms can also be substituted by >P— in the abovementioned unbranched or branched, acyclic or cyclic, aliphatic radicals. Polydentate, for example bidentate or tridentate, phosphine ligands are thus also comprised. These preferably comprise the group or >P—$CH_2CH_2$—P< or

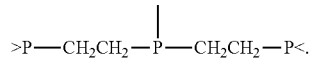

If the phosphine group comprises radicals other than the abovementioned unbranched or branched, acyclic or cyclic, aliphatic radicals, these generally correspond to those which are otherwise customarily used in phosphine ligands for metal-organic complex catalysts. Examples which may be mentioned are phenyl, tolyl and xylyl.

The metal-organic complex can comprise one or more, for example two, three or four, of the abovementioned phosphine groups having at least one unbranched or branched, acyclic or cyclic, aliphatic radical. The remaining ligands of the metal-organic complex can have various natures. Examples which may be mentioned are hydride, fluoride, chloride, bromide, iodide, formate, acetate, propionate, carboxylate, acetylacetonate, carbonyl, DMSO, hydroxide, trialkylamine, alkoxide.

The homogeneous catalysts can either be used directly in their active form or be generated only under reaction conditions from customary standard complexes such as [M(p-cymene)Cl$_2$]$_2$, [M(benzene)Cl$_2$]$_n$, [M(COD)(allyl)], [MCl$_3$× H$_2$O], [M(acetylacetonate)$_3$], [M(DMSO)$_4$Cl$_2$] where M is an element of group 8, 9 or 10 of the Periodic Table by addition of the corresponding phosphine ligand or ligands.

Homogeneous catalysts which are preferred in the process of the invention are [Ru(P″Bu$_3$)$_4$(H)$_2$], [Ru(P″octyl$_3$)$_4$(H)$_2$], [Ru(P″Bu$_3$)$_2$(1,2-bis(dicyclohexylphosphino)-ethane)(H)$_2$], [Ru(P″octyl$_3$)$_2$(1,2-bis(dicyclohexylphosphino)ethane) (H)$_2$], [Ru(PEt$_3$)$_4$(H)$_2$. By means of these, TOF (turnover frequency) values of greater than 1000 h$^{-1}$ can be achieved in the hydrogenation of carbon dioxide.

When homogeneous catalysts are used, the amount of the specified metal component in the metal-organic complex which is used is generally from 0.1 to 5000 ppm by weight, preferably from 1 to 800 ppm by weight and particularly preferably from 5 to 800 ppm by weight, in each case based on the total liquid reaction mixture in the hydrogenation reactor.

The partition coefficient of the homogeneous catalyst based on the amount of ruthenium in the amine phase and the product phase comprising the formic acid/amine adduct is in the range of P greater than 0.5, preferably greater than 1.0 and particularly preferably greater than 4, after the hydrogenation.

The tertiary amine to be used in the hydrogenation of carbon dioxide in the process of the invention has a boiling point which is at least 5° C. higher than that of formic acid. Here, as is customary, the boiling point of compounds have to be based on the same pressure in each case when the relative position of boiling points is indicated. The tertiary amine is selected or matched to the polar solvent so that the tertiary amine is present in enriched form in the upper phase in the hydrogenation reactor. For the present purposes, "in enriched form" means a proportion by weight of >50% of the free, i.e. not bound in the form of the formic acid/amine adduct, tertiary amine in the upper phase, based on the total amount of free, tertiary amine in the two liquid phases. The proportion by weight is preferably >90%. The tertiary amine is generally selected by means of a simple test in which the solubility of the desired tertiary amine in the two liquid phases under the planned process conditions is determined experimentally. The upper phase can additionally comprise amounts of the polar solvent and of a nonpolar inert solvent.

The tertiary amine to be used preferably has a boiling point which is at least 10° C. higher, particularly preferably at least 50° C. higher and very particularly preferably at least 100° C. higher, than that of formic acid. A restriction in terms of an upper limit to the boiling point is not necessary since a very low vapor pressure of the tertiary amine is in principle an advantage for the process of the invention. In general, the boiling point of the tertiary amine at a pressure of 1013 hPa abs, if necessary at a pressure extrapolated by known methods from vacuum to 1013 hPa abs, is below 500° C.

The tertiary amine which is preferably to be used in the process of the invention is an amine, comprising at least 12 carbon atoms per molecule, of the general formula (Ia)

$$NR^1R^2R^3 \quad \quad (Ia),$$

where the radicals $R^1$ to $R^3$ are identical or different and are each, independently of one another, an unbranched or branched, acyclic or cyclic, aliphatic, araliphatic or aromatic radical having in each case from 1 to 16 carbon atoms, preferably from 1 to 12 carbon atoms, where individual carbon atoms can also be substituted, independently of one another, by a hetero group selected from the group consisting of —O— and >N— or two or all three radicals can also be joined to one another to form a chain comprising at least four atoms in each case.

Examples of suitable amines are:

Tri-n-butylamine, tri-n-pentylamine, tri-n-hexylamine, tri-n-heptylamine, tri-n-octylamine, tri-n-nonylamine, tri-n-decylamine, tri-n-undecylamine, tri-n-dodecylamine, tri-n-tridecylamine, tri-n-tetradecylamine, tri-n-pentadecylamine, tri-n-hexadecylamine, tri(2-ethylhexyl)amine.

Dimethyldecylamine, dimethyldodecylamine, dimethyltetradecylamine, ethyldi(2-propyl)amine (bp$_{1013\ hPa}$=127° C.), dioctylmethylamine, dihexylmethylamine.

Tricyclopentylamine, tricyclohexylamine, tricycloheptylamine, tricyclooctylamine and derivatives thereof which are substituted by one or more methyl, ethyl, 1-propyl, 2-propyl, 1-butyl, 2-butyl or 2-methyl-2-propyl groups.

Dimethylcyclohexylamine, methyldicyclohexylamine, diethylcyclohexylamine, ethyldicyclohexylamine, dimethylcyclopentylamine, methyldicyclopentylamine.

Triphenylamine, methyldiphenylamine, ethyldiphenylamine, propyldiphenylamine, butyldiphenylamine, 2-ethylhexyldiphenylamine, dimethylphenylamine, diethylphenylamine, dipropylphenylamine, dibutylphenylamine, bis(2-ethylhexyl)phenylamine, tribenzylamine, methyldibenzylamine, ethyldibenzylamine and derivatives thereof which are substituted by one or more methyl, ethyl, 1-propyl, 2-propyl, 1-butyl, 2-butyl or 2-methyl-2-propyl groups.

N—$C_1$-$C_{12}$-alkylpiperidines, N,N-di-$C_1$-$C_{12}$-alkylpiperazines, N—$C_1$-$C_{12}$-alkylpyrrolidines, N—$C_1$-$C_{12}$-alkylimidazoles and derivatives thereof which are substituted by one or more methyl, ethyl, 1-propyl, 2-propyl, 1-butyl, 2-butyl or 2-methyl-2-propyl groups.

1,8-Diazabicyclo[5.4.0]undec-7-ene ("DBU"), 1,4-diazabicyclo[2.2.2]octane ("DABCO"), N-methyl-8-azabicyclo[3.2.1]octane ("tropane"), N-methyl-9-azabicyclo[3.3.1]nonane ("granatane"), 1-azabicyclo[2.2.2]octane ("quinuclidine").

It is naturally also possible to use mixtures of any amount of various tertiary amines in the process of the invention.

In the process of the invention, particular preference is given to using an amine of the general formula (Ia) in which the radicals $R^1$ to $R^3$ are selected independently from the group consisting of $C_1$-$C_{12}$-alkyl, $C_5$-$C_8$-cycloalkyl, benzyl and phenyl as tertiary amine.

Particular preference is given to using a saturated amine, i.e. only comprising single bonds, of the general formula (Ia) as tertiary amine in the process of the invention.

Very particular preference is given to using an amine of the general formula (Ia) in which the radicals $R^1$ to $R^3$ are selected independently from the group consisting of $C_5$-$C_8$-alkyl, in particular tri-n-pentylamine, tri-n-hexylamine, tri-n-heptylamine, tri-n-octylamine, dimethylcyclohexylamine, methyldicyclohexylamine, dioctylmethylamine and dimethyldecylamine, as tertiary amine in the process of the invention.

In particular, an amine of the general formula (Ia) in which the radicals $R^1$ to $R^3$ are selected independently from among $C_5$- and $C_6$-alkyl is used as tertiary amine.

The tertiary amine is preferably present in liquid form in all process stages of the process of the invention. However, this is not absolutely necessary. It would also be sufficient for the tertiary amine to be at least dissolved in suitable solvents. Suitable solvents are in principle those which are chemically inert in respect of the hydrogenation of carbon dioxide and the thermal dissociation of the adduct and in which the tertiary amine and, if a homogeneous catalyst is used, also the latter readily dissolve but do not readily dissolve the polar solvent and the formic acid/amine adduct. Possibilities are therefore in principle chemically inert, nonpolar solvents such as aliphatic, aromatic or araliphatic hydrocarbons, for example octane and higher alkanes, toluene, xylenes.

The polar solvent to be used in the hydrogenation of carbon dioxide in the process of the invention has a boiling point which is at least 5° C. lower than the temperature required for the dissociation of the formic acid/amine adducts at the same pressure. The polar solvent is to be selected or matched to the tertiary amine so that the polar solvent is present in enriched form in the lower phase. For the present purposes, "in enriched form" means a proportion by weight of >50% of the polar solvent in the lower phase based on the total amount of polar solvent in the two liquid phases. The proportion by weight is preferably >70%. The polar solvent is generally selected by means of a simple test in which the solubility of the desired polar solvent in the two liquid phases under the planned process conditions is determined experimentally.

The polar solvent can be a pure polar solvent or a mixture of various polar solvents, as long as the abovementioned conditions in respect of boiling point and phase behavior which the solvent has to meet are satisfied.

The polar solvent to be used preferably has a boiling point which is at least 10° C. lower, particularly preferably at least 50° C. lower, than the temperature required for dissociation of the formic acid/amine adducts at the same pressure. In the case of solvent mixtures, the boiling points of the solvent mixture used or an azeotrope or heteroazeotrope are at least 10° C. lower, particularly preferably at least 50° C. lower, than the temperature required for dissociation of the formic acid/amine adducts at the same pressure.

Classes of substances which are suitable as polar solvents are preferably alcohols and the formic esters thereof and water. The alcohols have a boiling point which is at least 10° C. lower, particularly preferably at least 50° C. lower, than the temperature required for dissociation of the formic acid/amine adducts at the same pressure in order to keep the esterification of the alcohols by formic acid very low.

As suitable alcohols, mention may be made of alcohols in the case of which the trialkylammonium formates preferentially dissolve in a mixture of the alcohol with water and this product phase has a miscibility gap with the free trialkylamine. Suitable alcohols are, for example, methanol, ethanol, 2-methoxyethanol, 1-propanol, 2-propanol, 1-butanol, 2-butanol, 2-methyl-1-propanol. The ratio of alcohol to water has to be selected so that together with the trialkylammonium formate and the trialkylamine a two-phase mixture in which the major part of the trialkylammonium formate, the water and the polar solvent are present in the lower phase is formed, which is generally determined by means of a simple test in which the solubility of the desired polar solvent mixture in the two liquid phases under the planned process conditions is determined experimentally.

The molar ratio of the polar solvent or solvent mixture to be used in the process of the invention to the tertiary amine used is generally from 0.5 to 30 and preferably from 1 to 20.

The carbon dioxide to be used in the hydrogenation of carbon dioxide can be used in solid, liquid or gaseous form. It is also possible to use industrially available gas mixtures comprising carbon dioxide as long as these are largely free of carbon monoxide (proportion by volume of <1% of CO). The hydrogen to be used in the hydrogenation of carbon dioxide is generally gaseous. Carbon dioxide and hydrogen can also comprise inert gases such as nitrogen or noble gases. However, the content of these is advantageously below 10 mol % based on the total amount of carbon dioxide and hydrogen in the hydrogenation reactor. Although larger amounts may likewise be tolerable, they generally require the use of a higher pressure in the reactor which in turn makes further compression energy necessary.

The hydrogenation of carbon dioxide is preferably carried out in the liquid phase at a temperature of from 20 to 200° C. and a total pressure of from 0.2 to 30 MPa abs. The temperature is preferably at least 30° C. and particularly preferably at least 40° C. and also preferably not more than 150° C., particularly preferably not more than 120° C. and very particularly preferably not more than 100° C. The total pressure is preferably at least 1 MPa abs and particularly preferably at least 5 MPa abs and also preferably not more than 30 MPa abs.

The partial pressure of carbon dioxide is generally at least 0.5 MPa and preferably at least 2 MPa and also generally not more than 8 MPa. The partial pressure of hydrogen is generally at least 0.5 MPa and preferably at least 1 MPa and also generally not more than 25 MPa and preferably not more than 10 MPa.

The molar ratio of hydrogen to carbon dioxide in the feed to the hydrogenation reactor is preferably from 0.1 to 10 and particularly preferably from 1 to 3.

The molar ratio of carbon dioxide to tertiary amine in the feed to the hydrogenation reactor is generally from 0.1 to 10 and preferably from 0.5 to 3.

As hydrogenation reactors, it is in principle possible to use all reactors which are suitable in principle for gas/liquid reactions at the given temperature and the given pressure. Suitable standard reactors for liquid-liquid reaction systems are indicated, for example, in K. D. Henkel, "Reactor Types and Their Industrial Applications", in Ullmann's Encyclopedia of Industrial Chemistry, 2005, Wiley-VCH Verlag GmbH & Co. KGaA, DOI: 10.1002/14356007.b04_087, chapter 3.3 "Reactors for gas-liquid reactions". Examples which may be mentioned are stirred tank reactors, tube reactors or bubble column reactors.

The hydrogenation of carbon dioxide in the process of the invention can be carried out batchwise or continuously. In the case of batch operation, the reactor is charged with the desired liquid and optionally solid starting materials and auxiliaries and carbon dioxide and hydrogen are subsequently introduced to the desired pressure at the desired temperature. After the reaction is complete, the reactor is generally depressurized and the two liquid phases which are formed are separated from one another. In the continuous mode of operation, the starting materials and auxiliaries including the carbon dioxide and hydrogen are introduced continuously. Accordingly, the liquid phase is continuously discharged from the reactor so that the average liquid level in the reactor remains constant. Preference is given to the continuous hydrogenation of carbon dioxide.

The average residence time in the hydrogenation reactor is generally from 10 minutes to 5 hours.

The formic acid/amine adducts formed in the hydrogenation of carbon dioxide in the presence of the catalyst to be used, the polar solvent and the tertiary amine generally have the general formula (IIa)

$$NR^1R^2R^3 \cdot x_i HCOOH \qquad (IIa),$$

where the radicals $R^1$ to $R^3$ correspond to the radicals described for the tertiary amine (Ia) and $x_i$ is from 0.4 to 5, preferably from 0.7 to 1.6. The respective average values of the amine-formic acid ratios in the product phases in the respective process steps, i.e. the factor $x_i$, can be determined, for example, by determining the formic acid content by titration with an alcoholic KOH solution against phenolphthalein and the amine content can be determined by gas chromatography. The composition of the formic acid/amine adducts, i.e. the factor $x_i$, can change during the various process steps. Thus, for example, adducts having a relatively high formic acid content with $x_2 > x_1$ and $x_2 = 1$ to 4 are generally formed after removal of the polar solvent, with the excess, free amine being able to form a second phase.

Two liquid phases are formed in the hydrogenation of carbon dioxide by the process of the invention. The lower phase is enriched with the formic acid/amine adducts and the polar solvent. With regard to the formic acid/amine adducts, "enriched" means a partition coefficient of the formic acid/amine adducts P=[concentration of formic acid/amine adduct (II) in liquid phase (A)]/[concentration of formic acid/amine adduct (II) in liquid phase (B)]

of >1. The partition coefficient is preferably 2 and particularly preferably 5. The upper phase is enriched with the tertiary amine. If a homogeneous catalyst is used, this is likewise present in enriched form in the upper phase.

The liquid phases (A) and (B) have the meaning defined above.

The two liquid phases formed are, in the process of the invention, separated from one another and the upper phase is recirculated to the hydrogenation reactor. Recirculation of a further liquid phase comprising unreacted carbon dioxide present in addition to the two abovementioned liquid phases and also of a gas phase comprising unreacted carbon dioxide and/or unreacted hydrogen to the hydrogenation reactor may also be advantageous. It may also be desirable, for example to discharge undesirable by-products or impurities, to discharge part of the upper phase and/or part of the carbon dioxide or liquid or gaseous phases comprising carbon dioxide and hydrogen from the process.

The two liquid phases are generally separated by gravimetric phase separation. As phase separation vessels, it is possible to use, for example, standard apparatuses and standard methods which are described, for example, in E. Müller et al., "Liquid-Liquid Extraction", in Ullmann's Encyclopedia of Industrial Chemistry, 2005, Wiley-VCH Verlag GmbH & Co. KGaA, DOI:10.1002/14356007.b03_06, chapter 3 "Apparatus". In general, the liquid phase enriched with the formic acid/amine adducts and the polar solvent is heavier and forms the lower phase.

The phase separation can be effected, for example, by depressurization, preferably to about or close to atmospheric pressure, and cooling of the liquid reaction mixture, for example to about or close to ambient temperature. However, there is a risk that at least part of the gas dissolved in the liquid phases at the higher reaction pressure, in particular carbon dioxide, will degas during the depressurization and have to be compressed separately as a gas stream and recirculated to the hydrogenation reactor. Likewise, the lower phase has to be brought separately to the reaction pressure before recirculation to the hydrogenation reactor. Here, a suitable compressor designed according to the pressure difference to be overcome or a pump, which also consumes additional energy in operation, has to be provided for each of the gas and liquid phases to be recirculated.

In the context of the present invention, it has been found that in the case of the present system, i.e. a lower phase enriched with the formic acid/amine adducts and the polar solvent and an upper phase enriched with the tertiary amine and in the case of the use of a homogeneous catalyst also with this, the two liquid phases can separate very well from one another even at a significantly elevated pressure. For this reason, the solvent in the process of the invention is preferably selected so that the separation of the lower phase enriched in the formic acid/amine adducts and the polar solvent from the upper phase in which with the tertiary amine and also the recirculation of the upper phase to the hydrogenation reactor can be carried out at a pressure of from 1 to 30 MPa abs. Depending on the total pressure in the hydrogenation reactor, the pressure is preferably not more than 30 MPa abs. It can even be possible to separate the two liquid phases from one another without prior depressurization and recirculate the upper phase to the hydrogenation reactor without an appreciable pressure increase. In this case, and also in the case of an only slight depressurization, it is possible to entirely dispense with recirculation of any gas phase. Whether this omission is possible for the respective specific system should be determined beforehand in the case of doubt by simple experimental examples.

The process of the invention can therefore preferably be carried out in such a way that the pressure and the temperature in the hydrogenation reactor and in the phase separation vessel are the same or approximately the same; for the present purposes, the same means a pressure difference of up to +/−5 bar or a temperature difference of up to +/−5° C.

In one embodiment the phase separation is carried out at a pressure of at least 50%, very particularly preferably at least 90% and in particular at least 95%, of the reaction pressure. The pressure in the phase separation is particularly preferably not more than 105% and very particularly preferably not more than 100% of the reaction pressure.

It has surprisingly also been found that in the case of the present system the two liquid phases separate very readily from one another even at an elevated temperature corresponding to the reaction temperature. In this case, no cooling is necessary for the phase separation and no subsequent heating of the upper phase to be recirculated is required, which likewise saves energy.

The major part of the polar solvent of the lower phase which has been separated off is separated off thermally from the formic acid/amine adducts in a distillation unit, with the polar solvent removed by distillation being recirculated to the hydrogenation reactor. The pure formic acid/amine adducts and free amine are obtained at the bottom of the distillation unit, since when the polar solvent is removed formic acid/amine adducts having a relatively low amine content are formed, as a result of which a two-phase bottoms mixture comprising an amine phase and a formic acid/amine adduct phase can be formed.

The thermal removal of the polar solvent or mixture, see above, is preferably carried out at a temperature at the bottom at which, at the given pressure, no free formic acid is formed from the formic acid/amine adduct having the higher (x1) or lower (x2) amine content. In general, the temperature at the bottom of the thermal separation unit is at least 20° C., preferably at least 50° C. and particularly preferably at least 70° C., and generally not more than 210° C., preferably not more than 190° C. The pressure is generally at least 1 hPa abs, preferably at least 50 hPa abs and particularly preferably at least 100 hPa abs, and generally not more than 1 MPa abs and preferably 0.1 MPa abs.

The thermal removal of the polar solvent or mixture is carried out either in an evaporator or in a distillation unit comprising vaporizer and column filled with ordered packing, random packing elements and/or trays. The solvent can be condensed after the thermal separation, with the enthalpy of condensation liberated once again being able to be utilized for, for example, preheating the solvent coming with amine/formic acid adduct mixture coming from the extraction to evaporation temperature.

As an alternative, only parts of the solvent mixture can be separated off. This applies in particular in the case of solvent components which can be separated off via a side stream in the later formic acid distillation. (Keyword: aqueous formic acid).

The formic acid/amine adducts which are obtained after the thermal removal of the polar solvent or mixture or parts of the solvent are then dissociated thermally into free formic acid and free tertiary amine in a distillation unit, with the free formic acid formed being removed by distillation and the free tertiary amine comprised in the bottoms from the distillation unit being recirculated to the hydrogenation reactor. Here, the free amine obtained as second phase in the thermal removal of the polar solvent can be separated off beforehand in a phase separation vessel, in a joint phase separation vessel be fed together with the bottom product from the thermal dissociation unit to the formic acid removal or as two-phase mixture directly to the dissociation unit (see general embodiments). The formic acid liberated can be taken off, for example, (i) at the top, (ii) at the top and as side offtake stream or (iii) only as side offtake stream. If formic acid is taken off at the top, a formic acid purity of up to 99.99% by weight is possible. When formic acid is taken off as side offtake stream, aqueous formic acid is obtained, with a mixture comprising about 85% by weight of formic acid being of particular importance here in industrial practice. Depending on the water content of the feed to the distillation unit, the majority of the formic acid is taken off as overhead product or as side product. If necessary, it is even possible to take off formic acid only as side product, in which case the required amount of water may be deliberately added. The thermal dissociation of the formic acid/amine adduct is generally carried out under the process parameters known from the prior art in respect of pressure, temperature and configuration of the apparatus. Thus, for example, reference may be made to the descriptions in EP 0 181 078 A or WO 2006/021,411. The distillation unit to be used generally comprises a distillation column which generally comprises random packing elements, ordered packings and/or trays.

In general, the temperature at the bottom of the distillation column is at least 130° C., preferably at least 140° C. and particularly preferably at least 150° C., and generally not more than 210° C., preferably not more than 190° C. and particularly preferably not more than 185° C. The pressure is generally at least 1 hPa abs, preferably at least 50 hPa abs and particularly preferably at least 100 hPa abs, and generally not more than 500 hPa abs, preferably not more than 300 hPa abs and particularly preferably not more than 250 hPa abs.

A water-comprising stream of formic acid is optionally taken off as side product. In the case of addition of water, for example to promote the hydrogenation, this is even particularly advantageous.

The solution of the adduct of tertiary amine and formic acid is extracted with streams of free tertiary amine coming from the appropriate phase separation vessels and recirculated to the hydrogenation reactor. This occurs in order to separate residual amounts of hydrogenation catalyst from the product stream. Without this extraction, hydrogenation catalyst could get into the apparatus for the thermal dissociation of the adduct of tertiary amine and formic acid, catalyze the decomposition of formic acid and thus reduce the yield of formic acid. Residual amounts of hydrogen and carbon dioxide are disposed of as offgas.

The extraction is carried out at temperatures of from 30 to 100° C. and pressures of from 1 to 80 bar. The extraction can also be carried out under hydrogen pressure.

The extraction of the hydrogenation catalyst can be carried out in any suitable apparatus known to those skilled in the art, preferably in countercurrent extraction columns, mixer-settler cascades or combinations of mixer-settlers with columns.

The product stream from the extraction apparatus, which comprises a solution of the formic acid/amine adduct in the respective solvent or solvent mixture, is fed into the thermal dissociation unit in order to separate the polar solvent or solvent mixture from the formic acid/amine adduct. The phase comprising tertiary amine and hydrogenation catalyst from the extraction apparatus is recirculated to the hydrogenation stage.

Apart from the catalyst, amounts of individual components of the polar solvent from the liquid phase to be extracted are sometimes dissolved in the extractant, viz. the amine stream. This is not a disadvantage for the process since the amount of solvent already extracted does not have to be fed to the solvent removal and may thus save vaporization energy.

It can be advantageous to integrate an apparatus for the adsorption of traces of hydrogenation catalyst between the extraction apparatus and the thermal separation apparatus. Numerous adsorbents are suitable for the adsorption. Examples are polyacrylic acid and salts thereof, sulfonated polystyrenes and salts thereof, activated carbons, montmorillonites, bentonites, silica gels and also zeolites.

If the amount of hydrogenation catalyst in the product stream from the phase separation vessel B is less than 1 ppm, in particular less than 0.1 ppm, the adsorption apparatus is sufficient for separating off and recovering the hydrogenation catalyst. The extraction stage can then be omitted and the tertiary amine can be recirculated together with the organic solvent to the hydrogenation stage.

Compared to the integrated processes which have previously been described in EP 181 078 B1 and EP 357 243 B1, the process of the invention has a series of advantages: the same tertiary amine is used for binding of the formic acid in the hydrogenation and thermal dissociation of the formic acid/amine adducts. This amine, which is obtained in free form in the thermal dissociation, is then used for extraction of catalyst residues from the product phase in order to recirculate traces of the catalyst together with the amine to the reaction vessel. It has a higher stability than the previously described N-alkylimidazoles. There are virtually no losses of noble metals. The catalyst is prevented from getting into the thermal dissociation unit and catalyzing the decomposition of formic acid therein. It is a great advantage that the catalyst is separated off in its active form and can be recirculated. High formic acid yields and a high product purity are achieved. Extractions and phase separations replace two distillations. This enables energy and capital costs to be reduced. In addition, the first phase separation can be carried out under superatmospheric pressure, which results in smaller offgas streams.

The invention will be illustrated below with the aid of examples and a drawing.

EXAMPLES

Examples A-1 to A-17 (Hydrogenation and Phase Separation, i.e. Process Step 1 of the Work-Up of the Output From the Hydrogenation Reactor (I))

A 250 ml autoclave made of Hastelloy C and provided with a magnetic stirrer bar was charged under inert conditions with tertiary amine, polar solvent and homogeneous catalyst. The autoclave was subsequently closed and $CO_2$ was injected at room temperature. $H_2$ was then injected and the reactor was heated while stirring (700 rpm). After the desired reaction time, the autoclave was cooled and the reaction mixture was depressurized. Unless indicated otherwise, a two-phase product mixture was obtained, with the upper phase being enriched with the still free tertiary amine and the homogeneous catalyst and the lower phase being enriched with the polar solvent and the formic acid/amine adduct formed. The total content of formic acid in the formic acid/amine adduct was determined by potentiometric titration with 0.1 N KOH in MeOH using a "Mettler Toledo DL50" titrator. The turnover frequency (=TOF; for the definition of the TOF see: J. F. Hartwig, *Organotransition Metal Chemistry*, 1st edition, 2010, University Science Books, *Sausalito/California* p. 545) and the reaction rate was calculated. The composition of the two phases was determined by gas chromatography. The ruthenium content was determined by atomic absorption spectroscopy (=AAS). The parameters and results of the individual experiments are shown in Tables 1.1 to 1.5.

Examples A-1 to A-17 show that, in the process of the invention, high to very high reaction rates of up to 0.98 mol $kg^{-1}$ $h^{-1}$ are achieved just by varying the tertiary amine, the polar solvent, the catalyst in respect of the ligands and the metal component, the amount of catalyst and the amount of water added. All systems examined formed two phases, with the upper phase in each case being enriched in the still free tertiary amine and the homogeneous catalyst and the lower phase in each case being enriched in the polar solvent and the formic acid/amine adduct formed.

TABLE 1.1

|  | Example A-1 | Example A-2 | Example A-3 | Example A-4 |
| --- | --- | --- | --- | --- |
| Tertiary amine | 75 g of trihexylamine | 75 g of trihexylamine | 75 g of tripentylamine | 75 g of tripentylamine |
| Polar solvent (used) | 17.8 g of 1-propanol<br>7.3 g of water | 21.7 g of 2-propanol<br>3.3 g of water | 17.8 g of 1-propanol<br>7.3 g of water | 17.8 g of 1-propanol<br>7.3 g of water |
| Catalyst | 0.2 g of $[Ru(P''Bu_3)_4(H)_2]$ | 0.2 g of $[Ru(P''Bu_3)_4(H)_2]$ | 0.3 g of $[Ru(P''Oct_3)_4(H)_2]$ | 0.2 g of $[Ru(P''Bu_3)_4(H)_2]$ |
| Injection of $CO_2$ | 19.6 g to 2.4 MPa abs | 20.0 g to 2.3 MPa abs | 20.0 g to 2.5 MPa abs | 20.3 g to 2.5 MPa abs |
| Injection of $H_2$ | To 10.4 MPa abs | To 10.3 MPa abs | To 10.6 MPa abs | To 10.5 MPa abs |
| Heating | To 50° C. | To 50° C. | To 50° C. | To 50° C. |
| Pressure change | To 10.0 MPa abs | To 10.5 MPa abs | To 11.4 MPa abs | To 11.5 MPa abs |
| Reaction time | 1 hour | 1 hour | 1 hour | 1 hour |
| Peculiarity | — | — | — | — |
| Upper phase | 57.5 g<br>8.0% of 1-propanol<br>0.9% of water<br>91.1% of trihexylamine | 62.3 g<br>15.4% of 2-propanol<br>1.7% of water<br>82.9% of trihexylamine | 75.6 g<br>10.9% of 1-propanol<br>0.9% of water<br>88.2% of tripentylamine | 63.8 g<br>5.7% of 1-propanol<br>0.5% of water<br>93.8% of tripentylamine |
| Lower phase | 43.6 g<br>5.9% of formic acid<br>30.3% of 1-propanol<br>15.6% of water<br>48.3% of trihexylamine | 37.3 g<br>4.7% of formic acid<br>32.4% of 2-propanol<br>5.9% of water<br>56.8% of trihexylamine | 22.9 g<br>3.4% of formic acid<br>41.7% of 1-propanol<br>28.9% of water<br>26% of tripentylamine | 38.4 g<br>6.8% of formic acid<br>36.7% of 1-propanol<br>18.2% of water<br>38.3% of tripentylamine |
| $k_{Ru}$ ($c_{Ru}$ in upper phase/$c_{Ru}$ in lower phase) | 1.60 | 1.02 | 85 | 2.7 |
| TOF | 252 h$^{-1}$ | 175 h$^{-1}$ | 81 h$^{-1}$ | 250 h$^{-1}$ |
| Reaction rate | 0.54 mol kg$^{-1}$ h$^{-1}$ | 0.38 mol kg$^{-1}$ h$^{-1}$ | 0.17 mol kg$^{-1}$ h$^{-1}$ | 0.56 mol kg$^{-1}$ h$^{-1}$ |

TABLE 1.2

|  | Example A-5 | Example A-6 | Example A-7 | Example A-8 |
| --- | --- | --- | --- | --- |
| Tertiary amine | 75 g of tripentylamine | 75 g of tripentylamine | 75 g of tripentylamine | 75 g tripentylamine |
| Polar solvent (used) | 21.8 g of 2-propanol<br>3.3 g of water | 17.8 g of 1-propanol<br>7.3 g of water | 17.8 g of 1-propanol<br>7.3 g of water | 18.8 g of methanol<br>6.3 g of water |
| Catalyst | 0.2 g of $[Ru(P''Bu_3)_4(H)_2]$ | 0.2 g of $[Ru(P''Bu_3)_4(H)_2]$, 0.2 g of 1,2-bis-dicyclohexyl-phosphinoethane | 0.2 g of $[Ru(P''Bu_3)_4(H)_2]$, 0.2 g of 1,2-bis-dicyclohexyl-phosphinoethane | 0.2 g of $[Ru(P''Bu_3)_4(H)_2]$ |
| Injection of $CO_2$ | 20.1 g to 2.4 MPa abs | 20.2 to 2.8 MPa abs | 20.0 to 2.5 MPa abs | 20.0 g to 2.3 MPa abs |
| Injection of $H_2$ | To 10.4 MPa abs | To 8.1 MPa abs | To 10.5 MPa abs | To 10.3 MPa |
| Heating | To 50° C. | To 50° C. | To 50° C. | To 50° C. |
| Pressure change | To 11.0 MPa abs | To 8.5 MPa abs | To 10.9 MPa abs. | To 10.5 MPa |
| Reaction time | 1 hour | 1 hour | 1 hour | 1 hour |
| Peculiarity | — | — | — | — |
| Upper phase | 65.7 g<br>11.5% of 2-propanol<br>1.0% of water<br>87.5 of tripentylamine | 60.6 g<br>5.1% of 1-propanol<br>94.9% of tripentylamine | 51.4 g<br>3.9% of 1-propanol<br>96.1% of tripentylamine | 60.5 g<br>3.1% of methanol<br>96.9% of tripentylamine |
| Lower phase | 35.0 g<br>5.6% of formic acid<br>40.6% of 2-propanol<br>7.5% of water<br>46.3% of tripentylamine | 40.8 g<br>7.0% of formic acid<br>36.0% of 1-propanol<br>17.9% of water<br>39.1% of tripentylamine | 50.1 g<br>8.4% of formic acid<br>31.5% of 1-propanol<br>14.6% of water<br>45.5% of tripentylamine | 40.8 g<br>7.3% of formic acid<br>41.5% of methanol<br>15.4% of water<br>35.8% of tripentylamine |
| $k_{Ru}$ ($c_{Ru}$ in upper phase/$c_{Ru}$ in lower phase) | 1.4 | 2.2 | 2.5 | 4.8 |
| TOF | 195 h$^{-1}$ | 282 h$^{-1}$ | 413 h$^{-1}$ | 290 h$^{-1}$ |
| Reaction rate | 0.43 mol kg$^{-1}$ h$^{-1}$ | 0.61 mol kg$^{-1}$ h$^{-1}$ | 0.90 mol kg$^{-1}$ h$^{-1}$ | 0.64 mol kg$^{-1}$ h$^{-1}$ |

TABLE 1.3

|  | Example A-9 | Example A-10 | Example A-11 | Example A-12 |
| --- | --- | --- | --- | --- |
| Tertiary amine | 70 g of trihexylamine | 75 g of tripentylamine | 75 g of tripentylamine | 75 g of trihexylamine |
| Polar solvent (used) | 15.0 g of ethanol<br>5.0 g of water | 21.5 g of methanol<br>3.6 g of water | 24.0 g of methanol<br>1.0 g of water | 22.0 g of methanol<br>3.0 g of water |
| Catalyst | 0.2 g of $[Ru(P''Bu_3)_4(H)_2]$ | 0.2 g of $[Ru(P''Bu_3)_4(H)_2]$ | 0.16 g of $[Ru(P''Oct_3)_4(H)_2]$ | 0.16 g of $[Ru(P''Oct_3)_4(H)_2]$, 0.08 g of 1,2-bis(dicyclohexylphosphino)-ethane |
| Injection of $CO_2$ | 20.2 g to 2.5 MPa abs | 20.0 g to 2.2 MPa abs | 19.9 g to 2.3 MPa abs | 20.0 g to 2.5 MPa abs |
| Injection of $H_2$ | To 10.9 MPa abs | To 10.5 MPa abs | To 10.3 MPa abs | To 10.5 MPa abs |
| Heating | To 50° C. | To 50° C. | To 50° C. | To 50° C. |
| Pressure change | To 11.8 MPa abs | To 10.3 MPa abs | To 10.2 MPa abs | To 10.6 MPa abs |
| Reaction time | 1 hour | 1 hour | 1 hour | 1 hour |
| Peculiarity | — | — | — | — |

TABLE 1.3-continued

|  | Example A-9 | Example A-10 | Example A-11 | Example A-12 |
|---|---|---|---|---|
| Upper phase | 52.0 g<br>4.6% of ethanol<br>95.4% of trihexylamine | 49.5 g<br>2.5% of methanol<br>77.5 g of tripentylamine | 63.3 g<br>8.4% of methanol<br>91.6% of tripentylamine | 46.7 g<br>4.1% of methanol<br>95.9% of trihexylamine |
| Lower phase | 38.4 g<br>7.3% of formic acid<br>32.8% of ethanol<br>13.0% of water<br>46.9% of tripentylamine | 52.8 g<br>8.7% of formic acid<br>38.5% of methanol<br>6.8% of water<br>46.0% of tripentylamine | 35.9 g<br>4.5% of formic acid<br>52.1% of methanol<br>2.8% of water<br>40.7% of tripentylamine | 54.2 g<br>7.2% of formic acid<br>37.1% of methanol<br>5.5% of water<br>50.2% of trihexylamine |
| $k_{Ru}$ ($c_{Ru}$ in upper phase/ $c_{Ru}$ in lower phase) | 1.9 | 2.5 | 14.0 | 1.7 |
| TOF | 271 h$^{-1}$ | 446 h$^{-1}$ | 343 h$^{-1}$ | 806 h$^{-1}$ |
| Reaction rate | 0.67 mol kg$^{-1}$ h$^{-1}$ | 0.98 mol kg$^{-1}$ h$^{-1}$ | 0.35 mol kg$^{-1}$ h$^{-1}$ | 0.84 mol kg$^{-1}$ h$^{-1}$ |

TABLE 1.4

|  | Example A-13 | Example A-14 | Example A-15 | Example A-16 |
|---|---|---|---|---|
| Tertiary amine | 75 g of trihexylamine | 75 g of trihexylamine | 75 g of trihexylamine | 75 g of trihexylamine |
| Polar solvent (used) | 24.0 g of methanol<br>6.7 g of water | 25.0 g of ethanol<br>6.0 g of water | 25.0 g of 1-propanol<br>6.0 g of water | 25.0 g of ethanol<br>8.0 g of water |
| Catalyst | 0.18 g of<br>[Ru(PnBu3)4(H)2] | 0.16 g of<br>[Ru(PnOct3)4(H)2],<br>0.08 g of 1,2-bis(dicyclohexyl-phosphino)ethane | 0.16 g of<br>[Ru(PnOct3)4(H)2],<br>0.08 g of 1,2-bis(dicyclohexyl-phosphino)ethane | 0.16 g of<br>[Ru(PnOct3)4(H)2],<br>0.08 g of 1,2-bis(dicyclohexyl-phosphino)ethane |
| Injection of $CO_2$ | 20.2 g to 3.5 MPa abs | 19.9 g to 2.5 MPa abs | 19.9 g to 2.5 MPa abs | 19.5 g to 2.6 MPa abs |
| Injection of $H_2$ | To 11.5 MPa abs | To 11.5 MPa abs | To 10.5 MPa abs | To 10.7 MPa abs |
| Heating | To 50° C. | To 50° C. | To 50° C. | To 50° C. |
| Pressure change | To 11.0 MPa abs | To 10.5 MPa abs | To 11.3 MPa abs | To 11.6 MPa abs |
| Reaction time | 1 hour | 1 hour | 1 hour | 2 hours |
| Peculiarity | — | — | — | — |
| Upper phase | 44.1 g<br>2.7% of methanol<br>97.3% of trihexylamine | 60.2 g<br>0.7% of water<br>6.6% of ethanol<br>92.7% of trihexylamine | 46.4 g<br>2.0% of water<br>6.2% of 1-propanol<br>91.8% of trihexylamine | 48.9 g<br>0.6% of water<br>4.5% of ethanol<br>94.9% of trihexylamine |
| Lower phase | 65.9 g<br>7.5% of formic acid<br>10.2% of water<br>34.6% of methanol<br>47.7% of trihexylamine | 51.3 g<br>5.3% of formic acid<br>9.3% of water<br>41.0% of ethanol<br>44.4% of trihexylamine | 60.6 g<br>5.6% of formic acid<br>8.4% of water<br>36.5% of 1-propanol<br>49.5% of trihexylamine | 61.9 g<br>6.0% of formic acid<br>12.4% of water<br>36.8% of ethanol<br>44.8% of trihexylamine |
| $k_{Ru}$ ($c_{Ru}$ in upper phase/ $c_{Ru}$ in lower phase) | 1.9 | 1.6 | 1.5 | 3.2 |
| TOF | 551 h$^{-1}$ | 569 h$^{-1}$ | 726 h$^{-1}$ | 351 h$^{-1}$ |
| Reaction rate | 0.98 mol kg$^{-1}$ h$^{-1}$ | 0.53 mol kg$^{-1}$ h$^{-1}$ | 0.68 mol kg$^{-1}$ h$^{-1}$ | 0.37 mol kg$^{-1}$ h$^{-1}$ |

TABLE 1.5

|  | Example A-17 |
|---|---|
| Tertiary amine | 75 g of trihexylamine |
| Polar solvent (used) | 25.0 g of 1-propanol<br>8.0 g of water |
| Catalyst | 0.16 g of [Ru(P"Oct$_3$)$_4$(H)$_2$],<br>0.08 g of 1,2-bis(dicyclohexyl-phosphino)ethane |
| Injection of $CO_2$ | 20.3 g to 2.5 MPa abs |
| Injection of $H_2$ | To 10.5 MPa abs |
| Heating | To 50° C. |
| Pressure change | To 11.4 MPa abs |
| Reaction time | 2 hours |
| Peculiarity | — |
| Upper phase | 37.1 g<br>2.6% of water<br>3.9% of 1-propanol<br>93.5% of trihexylamine |
| Lower phase | 74.5 g<br>6.2% of formic acid<br>9.4% of water<br>31.5% of 1-propanol<br>52.9% of trihexylamine |
| $k_{Ru}$ ($c_{Ru}$ in upper phase/ $c_{Ru}$ in lower phase) | 3.9 |
| TOF | 437 h$^{-1}$ |
| Reaction rate | 0.45 mol kg$^{-1}$ h$^{-1}$ |

Examples B1-3 (Extraction of the Catalyst)

A 100 ml autoclave made of Hastelloy C and provided with a blade stirrer was charged under inert conditions with the trialkylamine, polar solvent and the catalyst. The autoclave was subsequently closed and $CO_2$ was injected at room temperature. $H_2$ was then injected and the reactor was heated while stirring (1000 rpm). After the reaction time, the autoclave was cooled and the reaction mixture was depressurized. A two-phase product mixture was obtained, with the upper phase being enriched in the still free tertiary amine and the homogeneous catalyst and the lower phase being enriched in the polar solvent and the formic acid/amine adduct formed. The lower phase was separated off and admixed three times under inert conditions with the same amount (mass of amine corresponds to the mass of the lower phase) of free trialkylamine (stirring for 10 minutes at room temperature and subsequently separating the phases) for extraction of the catalyst.

The total content of formic acid in the formic acid/amine adduct was determined by potentiometric titration with 0.1 N KOH in MeOH using a "Mettler Toledo DL50" titrator. The ruthenium content was determined by AAS. The parameters and results of the individual experiments are shown in Table 1.6.

Examples B-1 to B-3 show that, in the process of the invention, the amount of ruthenium catalyst in the product phase can be reduced by extraction with tertiary amine obtained in process step 5). This value could be reduced further by means of further extraction steps or a continuous countercurrent extraction.

TABLE 1.6

|  | Example B-1 | Example B-2 | Example B-3 |
|---|---|---|---|
| Tertiary amine | 37.5 g of trihexylamine | 37.5 g of tripentylamine | 37.5 g of trihexylamine |
| Polar solvent (used) | 12.0 g of methanol | 10.0 g of methanol | 10.0 g of methanol |
|  | 0.5 g of water | 2.5 g of water | 2.5 g of water |
| Catalyst | 0.16 g of $[Ru(PnOctyl_3)_4(H)_2]$ | 0.1 g of $[Ru(PnButyl_3)_4(H)_2]$ | 0.1 g of $[Ru(PnButyl_3)_4(H)_2]$ |
| Injection of $CO_2$ | To 1.7 MPa abs | To 2.3 MPa abs | To 2.5 MPa abs |
| Injection of $H_2$ | To 8.0 MPa abs | To 8.0 MPa abs | To 8.0 MPa abs |
| Heating | 50° C. | 50° C. | 50° C. |
| Reaction time | 1.5 hours | 1 hour | 1 hour |
| Upper phase | 23.3 g | 31.1 g | 22.9 g |
| Lower phase | 26.2 g | 17.4 g | 27.5 g |
|  | 6.1% of formic acid | 5.6% of formic acid | 7.2% of formic acid |
| $c_{Ru}$ in upper phase after reaction | 350 ppm | 320 ppm | 250 ppm |
| $c_{Ru}$ in lower phase after reaction | 33 ppm | 80 ppm | 170 ppm |
| $c_{Ru}$ in lower phase after extraction | 21 ppm | 50 ppm | 75 ppm |

Examples C1-C4 (Thermal Separation of the Polar Solvent From the Trialkylamine/Solvent/Formic Acid Mixtures Present as Product Phase After the Extraction)

Alcohol and water are distilled off from the product phase (comprises the formic acid/amine adduct) under reduced pressure by means of a rotary evaporator. A two-phase mixture (trialkylamine phase and formic acid/amine adduct phase) is formed as bottoms, the two phases are separated and the formic acid content of the lower phase is determined by potentiometric titration with 0.1 N KOH in MeOH using a "Mettler Toledo DL50" titrator. The amine content and alcohol content are determined by gas chromatography. The parameters and results of the individual experiments are shown in Table 1.7.

Examples C-1 to C-4 show that, in the process of the invention, various polar solvents can be separated off from the product phase under mild conditions to form a lower phase which is relatively rich in formic acid and an upper phase which comprises predominantly tertiary amine.

TABLE 1.7

|  | Example C-1 | Example C-2 | Example C-3 | Example C-4 |
|---|---|---|---|---|
| Feed mixture (% by weight) | 18.7 g | 19.3 g | 81.8 g | 88.6 g |
|  | 7.2% of formic acid | 5.8% of formic acid | 7.3% of formic acid | 9.2% of formic acid |
|  | 26.4% of 1-propanol | 22.8% of 2-propanol | 41.3% of methanol | 31.4% of ethanol |
|  | 15.5% of water | 4.1% of water | 15.4% of water | 11.3% of water |
|  | 48.3% of trihexylamine | 67.2% of trihexylamine | 35.9% of tripentylamine | 48.1% of tripentylamine |
| Formic acid:amine feed mixture | 1:1.2 | 1:2.0 | 1:1 | 1:1.1 |
| Pressure | 20 mbar | 20 mbar | 200 mbar | 200 mbar |
| Temperature | 50° C. | 50° C. | 100° C. | 110° C. |
| Formic acid content of lower phase after distillation (% by weight) | 16.4% | 18.0% | 23.7% | 22.7% |
| Formic acid:amine in lower phase after distillation (molar ratio) | 1:0.76 | 1:0.78 | 1:0.6 | 1:0.56 |
| Recovery of formic acid after distillation | 95.3% | 93.7% | 90.4% | 95.2% |

Examples D1 and D2 (Thermal Separation of the Polar Solvent From the Trialkylamine/Solvent/Formic Acid Mixtures and Dissociation of the Formic Acid/Amine Adduct)

Alcohol and water are distilled off from the product phase (comprises the formic acid/amine adduct) under reduced pressure by means of a rotary evaporator. A two-phase mixture (trialkylamine phase and formic acid/amine adduct phase) is formed as bottoms and the two phases are separated. The composition of the distillates (comprising the major part of the methanol and of the water), of the upper phase (comprising the free trialkylamine) and of the lower phase (comprising the formic acid/amine adduct) was determined by gas chromatography and by potentiometric titration of the formic acid against 0.1 N KOH in MeOH using a "Mettler Toledo DL50" titrator. The formic acid is then thermally dissociated from the trialkylamine in the lower phase from the first step in a vacuum distillation apparatus comprising a 10 cm Vigreux column. After the formic acid has been completely split off, a single-phase bottom product comprising the pure trialkylamine is obtained and can be used for extraction of the catalyst and recirculation to the hydrogenation. The formic acid and residual water are present in the distillate. The composition of the bottoms and of the distillate was determined by gas chromatography and by potentiometric titration of the formic acid against 0.1 N KOH in MeOH using a "Mettler Toledo DL50" titrator. The parameters and results of the individual experiments are shown in Table 1.8.

Examples D-1 and D-2 show that, in the process of the invention, various polar solvents can be separated off from the product phase under mild conditions, with a lower phase which is relatively rich in formic acid and an upper phase comprising predominantly tertiary amine being formed. The formic acid can then be dissociated from the trialkylamine in this lower phase which is relatively rich in formic acid at elevated temperatures giving the free trialkylamine. The formic acid obtained in this way still comprises a little water, but this can be separated off from the formic acid by means of a column having a relatively high separation power. The trialkylamine obtained both in the removal of the solvent and in the thermal dissociation can be used for removing the catalyst from the product stream in process step 2).

Figure 2:
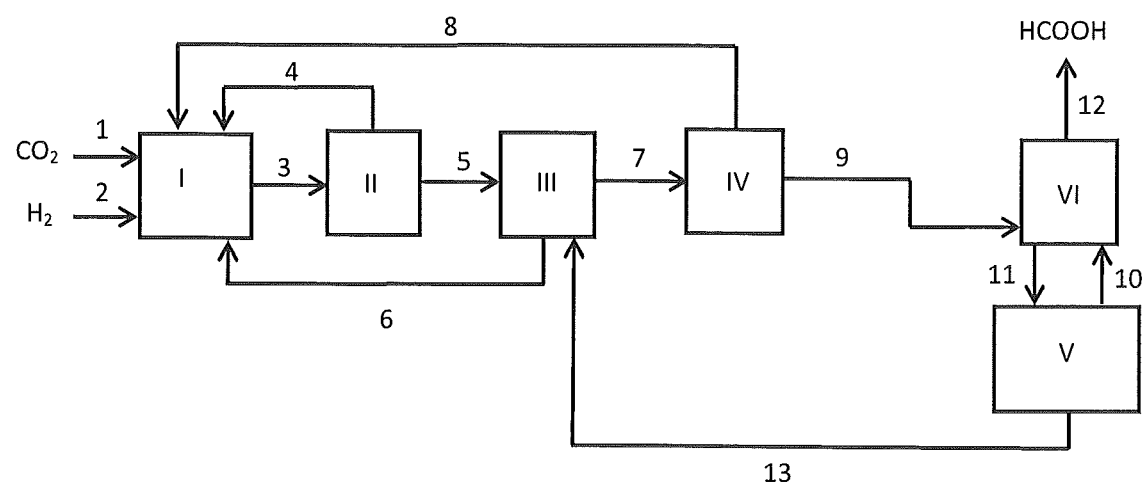
FIG. 2 illustrates a block diagram of a further preferred embodiment of the process of the invention.
Figure 3:
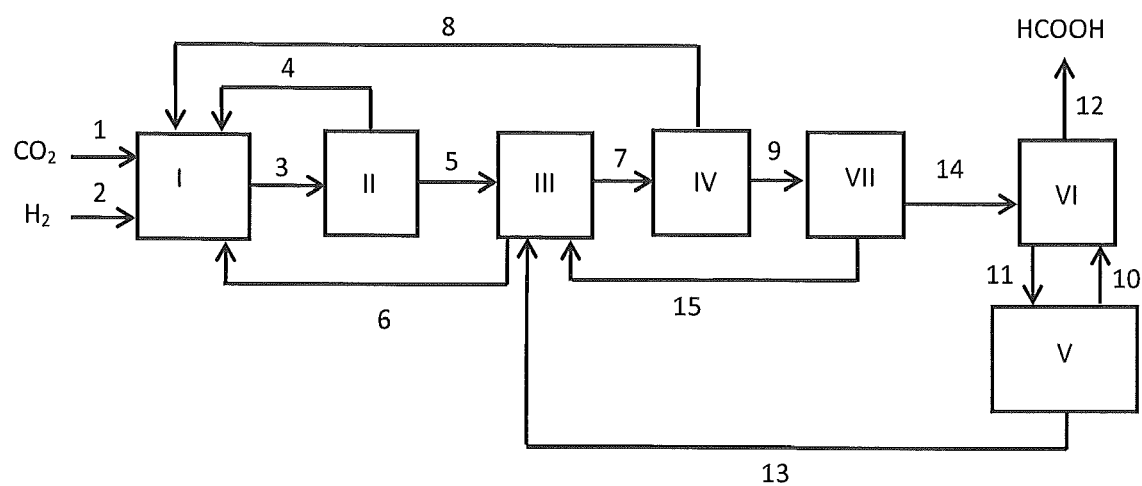
FIG. 3 illustrates a block diagram of an additional preferred embodiment of the process of the invention.

The drawings specifically show:

FIG. 1 a block diagram of a preferred embodiment of the process of the invention, FIG. 2 a block diagram of a further preferred embodiment of the process of the invention and FIG. 3 a block diagram of an additional preferred embodiment of the process of the invention.

In the embodiment as per FIG. 1, carbon dioxide, stream 1, and hydrogen, stream 2, are fed into the hydrogenation reactor I. In the reactor, the two streams are reacted in the presence of a catalyst comprising an element of group 8, 9 or 10 of the Periodic Table, a tertiary amine and a polar solvent to give a formic acid/amine adduct. Two liquid phases are formed here. The lower phase is enriched in the formic acid/amine adducts and the polar solvent, and the upper phase is enriched in the tertiary amine and, when a homogeneous catalyst is used, this too. The two liquid phases are fed to a phase separator II (stream 3) and separated from one another. The upper phase 4 is recirculated to the hydrogenation reactor I. The lower phase 5 is fed to an extraction apparatus III in which catalyst residues are extracted with the tertiary amine from the phase separation vessel V. The tertiary amine together with the catalyst residues (stream 6) from the extraction unit III is then recirculated to the hydrogenation reactor I. The product phase 7 from the extraction unit III is fed to the thermal separation unit IV in order to separate off the polar solvent thermally from the formic acid/amine adducts. Stream 7 can be conveyed beforehand through an adsorbent bed in order to remove last traces of ruthenium from this stream. The polar solvent which is separated off thermally in the unit IV is recirculated as stream 8 to the hydrogenation reactor I and the two-phase mixture from the bottom of the thermal separation unit IV, comprising the formic acid/amine adducts and the tertiary amine (stream 9), is fed to the phase separation vessel V. The formic acid/amine adducts are separated off in the phase separation vessel V and fed as stream 10 to the distillation unit VI in which this stream 10 is thermally dissociated into free formic acid and tertiary amine. The free formic acid is, for example, removed as overhead product, stream 12. The two-phase bottoms from the distillation unit VI, comprising tertiary amine and undissociated formic acid/amine adducts, stream 11, is fed back to the phase separation vessel V. The

TABLE 1.8

|  | Example D-1a (removal of the polar solvent) | Example D-1b (dissociation of the formic acid/amine adduct) | Example D-2a (removal of the polar solvent) | Example D-2b (dissociation of the formic acid/amine adduct) |
| --- | --- | --- | --- | --- |
| Feed mixture (% by weight) | 199.8 g 8.9% of formic acid 28.4% of methanol 5.6% of water 57.1% of trihexylamine | Lower phase from D1-a | 199.8 g 7.8% of formic acid 33.0% of methanol 15.1% of water 44.0% of trihexylamine | Lower phase from D2-a |
| Formic acid:amine in feed mixture | 1:1.1 | 1:0.64 | 1:1 | 1:0.89 |
| Pressure | 200 mbar | 90 mbar | 200 mbar | 90 mbar |
| Temperature | 120° C. | 153° C. | 120° C. | 153° C. |
| Lower phase in the bottoms after distillation (% by weight) | 79.8 g 22.1% of formic acid 1.5% of water 76.4% of trihexylamine | 63.6 g 100% of trihexylamine | 69.4 g 14.9% of formic acid 6.9% of water 78.2% of trihexylamine | 55.5 g 99.7% of trihexylamine 0.3% of water |
| Upper phase in the bottoms after distillation | 50.5 g 100% of trihexylamine | Single-phase | 32.7 g 99.7% of trihexylamine 0.3% of water | Single-phase |
| Distillate | 66.6 g 0.3% of formic acid 81.2% of methanol 18.5% of water | 14.9 g 92.1% of formic acid 7.9% of water | 93.1 g 70.1% of methanol 29.9% of water | 12.9 g 85.0% of formic acid 15% of water | tertiary amine which is separated off in the phase separation vessel V is fed to the extraction unit III in order to extract catalyst residues.

In the embodiment as per FIG. 2, carbon dioxide 1 and hydrogen 2 are fed into the hydrogenation reactor I. In this reactor, they are reacted in the presence of a catalyst comprising an element of group 8, 9 or 10 of the Periodic Table, a tertiary amine and a polar solvent to give formic acid/amine adducts. Two liquid phases are formed here. The lower phase is enriched in the formic acid/amine adducts and the polar solvent, and the upper phase is enriched with the tertiary amine and, when a homogeneous catalyst is used, this too. The two liquid phases (stream 3) are fed to a phase separator II and separated from one another. The upper phase is recirculated to the hydrogenation reactor I (stream 4). The lower phase is fed to an extraction apparatus III in which catalyst residues are extracted with the tertiary amine from the phase separation vessel V. The tertiary amine together with the catalyst residues from the extraction unit III is then recirculated to the hydrogenation reactor I (stream 6). The product phase 7 from the extraction unit III is fed to the thermal separation unit IV in order to separate off the polar solvent thermally from the formic acid/amine adducts. Stream 7 can be passed beforehand through an adsorbent bed in order to remove last traces of catalyst from this stream. The polar solvent which is thermally separated off in the unit IV is recirculated as stream 8 to the hydrogenation reactor I and the two-phase mixture from the bottom of the thermal separation unit IV, comprising the formic acid/amine adducts and the tertiary amine, stream 9, is fed as stream 10 to the distillation unit VI. In this, the formic acid/amine adducts are thermally dissociated into free formic acid and tertiary amine. The free formic acid is, for example, removed as overhead product, stream 12. The two-phase bottoms from the distillation unit VI, stream 11, comprising tertiary amine and undissociated formic acid/amine adducts, are fed to the phase separation vessel V. The tertiary amine which is separated off in the phase separation vessel V is fed as stream 13 to the extraction unit III in order to extract catalyst residues. Part of stream 13 can also be recirculated directly to the hydrogenation reactor if not all of the amine is required for the extraction.

In the embodiment as per FIG. 3, carbon dioxide 1 and hydrogen 2 are fed to the hydrogenation reactor I. In this reactor, they are reacted in the presence of a catalyst comprising an element of 8, 9 or 10 of the Periodic Table, a tertiary amine and a polar solvent to give formic acid/amine adducts. Two liquid phases are formed here. The lower phase is enriched in the formic acid/amine adducts and the polar solvent, and the upper phase is enriched in the tertiary amine and, when a homogeneous catalyst is used, this too. The two liquid phases are fed as stream 3 to a phase separator II and separated from one another. The upper phase, stream 4, is recirculated to the hydrogenation reactor I. The lower phase, stream 5, is fed to an extraction apparatus III in which catalyst residues are extracted with the tertiary amine from the phase separation vessel IV and V. The tertiary amine together with the catalyst residues from the extraction unit III is then recirculated to the hydrogenation reactor I. The product phase 7 from the extraction unit III is fed to the thermal separation unit V in order to separate off the polar solvent thermally from the formic acid/amine adducts. Stream 7 can be conveyed beforehand through an adsorbent bed in order to remove last traces of ruthenium from this stream. The polar solvent which is separated off thermally in the unit IV is recirculated to the hydrogenation reactor I (stream 8) and the two-phase mixture from the bottom of the distillation unit IV, comprising the formic acid/amine adducts and the tertiary amine, stream 9, is fed to the phase separation vessel VII. The tertiary amine which is separated off in the phase separation vessel VII is fed to the extraction unit III. The formic acid/amine adducts from the phase separation vessel VII are fed to the distillation unit VI. In this, the formic acid/amine adducts are thermally dissociated into free formic acid and tertiary amine. The free formic acid is, for example, removed as overhead product, stream 12. The two-phase bottoms from the distillation unit VI, comprising tertiary amine and undissociated formic acid/amine adducts, stream 11, are fed to the phase separation vessel V. The tertiary amine which is separated off in the phase separation vessel V is fed as stream 13 to the extraction unit III in order to extract catalyst residues.

The process of the invention makes it possible to obtain concentrated formic acid in high yield and high purity by hydrogenation of carbon dioxide. In particular, it provides a particularly simple mode of operation which compared to the prior art has a simpler process concept, simpler process stages, a smaller number of process stages and simpler apparatuses. Thus, for example, if the tertiary amine and the polar solvent are appropriately selected in the case of the use of a homogeneous catalyst, the latter is separated off from formic acid/amine adducts by phase separation and recirculated without further work-up steps to the hydrogenation reactor. The phase separation can also be carried out under superatmospheric pressure. The prompt separation of the catalyst from the formic acid/amine adducts formed suppresses a backreaction with decomposition into carbon dioxide and hydrogen. In addition, losses of catalyst and thus losses of noble metal are minimized by the retention or removal of the catalyst as a result of the formation of two liquid phases. In addition, catalyst remaining in the product stream can be virtually completely recirculated to the hydrogenation reactor as a result of the extraction with the free amine from the thermal dissociation units, which further minimizes the losses of noble metal and is a very great advantage for an economical process and also largely suppresses the decomposition of the formic acid in the thermal dissociation units. Furthermore, no complicated separate base replacement is required in the process of the invention, so that the formic acid/amine adducts formed in the hydrogenation reactor can be used directly for the thermal dissociation. The use of a low-boiling polar solvent makes it possible for this to be separated off thermally under mild conditions in a stage preceding the thermal dissociation of the formic acid, as a result of which the esterification of alcohols used and decomposition of the formic acid are minimized, a lower energy consumption is necessary and a higher purity of the formic acid can be achieved. The simpler process concept makes it possible for the production plant required for carrying out the process of the invention to be made more compact in the sense of a smaller space requirement and the use of fewer apparatuses compared to the prior art. It has a lower capital cost requirement and a lower energy consumption.

The invention claimed is:

1. A process for preparing formic acid which comprises reacting carbon dioxide with hydrogen in a hydrogenation reactor in the presence of
    a catalyst comprising an element of group 8, 9 or 10 of the Periodic Table,
    a tertiary amine comprising at least 12 carbon atoms per molecule and
    a polar solvent comprising one or more monoalcohols selected from among methanol, ethanol, propanols and butanols and also water, to form formic acid/amine adducts as intermediates which are subsequently thermally dissociated, where a tertiary amine which has a boiling point at least 5° C. higher than that of formic acid and two liquid phases are formed in the reaction in the hydrogenation reactor, namely a lower phase which comprises predominantly the polar solvent and in which the formic acid/amine adducts are present in enriched form and an upper phase which comprises predominantly the tertiary amine and in which the catalyst is present in enriched form,
wherein
the work-up of the output from the hydrogenation reactor is carried out by the following process steps:
1) separating the two liquid phases from the hydrogenation reactor in a phase separation vessel, recirculation of the upper phase from the phase separation vessel to the hydrogenation reactor and passing-on of the lower phase from the phase separation vessel to an extraction apparatus in which
2) extracting residues of catalyst with the same tertiary amine which was used in the hydrogenation and the catalyst-laden tertiary amine is recycled to the hydrogenation reactor and the catalyst-free stream of polar solvent loaded with the formic acid/amine adducts is passed on to a distillation unit in which
3) separating off the polar solvent as overhead stream and recycling to the hydrogenation reactor to give a stream which
4) is separated in a phase separation vessel into an upper phase comprising predominantly the tertiary amine and a lower phase comprising predominantly the formic acid/amine adducts, where
5) the lower phase from the phase separation vessel is fed to a thermal dissociation unit and dissociated therein into a stream which comprises the tertiary amine and is recirculated to the phase separation vessel and pure formic acid and
   a stream comprising the tertiary amine is conveyed from the phase separation vessel into the extraction apparatus as selective solvent for the catalyst.

2. The process according to claim 1, wherein an amine of the general formula (Ia)

$$NR^1R^2R^3 \quad (Ia)$$

where the radicals $R^1$ to $R^3$ are identical or different and are each, independently of one another, an unbranched or branched, acyclic or cyclic, aliphatic, araliphatic or aromatic radical having in each case from 1 to 6 carbon atoms, where individual carbon atoms can also be substituted, independently of one another, by a hetero group selected from the group consisting of O and >N or two or all three radicals can also be joined to one another to form a chain comprising at least four atoms in each case, is used as tertiary amine, with the proviso that the tertiary amine comprises at least 12 carbon atoms per molecule.

3. The process according to claim 2, wherein the radicals $R^1$ to $R^3$ are selected independently from the group consisting of C1-C12-alkyl, C5-C8-cycloalkyl, benzyl and phenyl.

4. The process according to claim 2, wherein a saturated amine of the general formula (Ia) is used as tertiary amine.

5. The process according to claim 2, wherein the radicals $R^1$ to $R^3$ are selected independently from C5 and C6-alkyl.

6. The process according to claim 1, wherein methanol and/or ethanol are used as polar solvent.

7. The process according to claim 5, wherein methanol and/or ethanol are used as polar solvent.

8. The process according to claim 1, wherein the polar solvent comprises up to 50% by weight of water.

9. The process according to claim 1, wherein the polar solvent comprises up to 50% by weight of water.

10. The process according to claim 1, wherein the catalyst is a homogeneous catalyst.

11. The process according to claim 10, wherein the homogeneous catalyst is a metal-organic complex comprising an element of group 8, 9 or 10 of the Periodic Table and at least one phosphine group having at least one unbranched or branched, acyclic or cyclic aliphatic radical having from 1 to 12 carbon atoms, with individual carbon atoms also being able to be substituted by >P—.

12. The process according to claim 1, wherein the reaction in the hydrogenation reactor is carried out at a temperature in the range from 20 to 200° C. and a pressure in the range from 0.2 to 30 MPa abs.

13. The process according to claim 12, wherein the pressure in the hydrogenation reactor and in the phase separation vessel is the same or approximately the same.

14. The process according to claim 12, wherein the temperature in the hydrogenation reactor and in the phase separation vessel is the same.

15. The process according to claim 13, wherein the temperature in the hydrogenation reactor and in the phase separation vessel is the same.

* * * * *